United States Patent [19]
Milo, Jr. et al.

[11] Patent Number: 5,830,656
[45] Date of Patent: Nov. 3, 1998

[54] DETECTING THE EXPRESSION OF THE CATR1 GENE IN SQUAMOUS CELL CARCINOMA

[75] Inventors: George E. Milo, Jr.; Bruce C. Casto, both of Columbus; Dawei Li, Dublin; Jucheng Chen, Columbus, all of Ohio; Charles F. Shuler, West Lake Village, Calif.; Martin L. Ribovich, Columbus, Ohio; Inge Noyes, Galena, Ohio; Xioa Li Sun, Columbus, Ohio; Karl S. Theil, Dublin, Ohio

[73] Assignee: The Ohio State Research Foundation, Columbus, Ohio

[21] Appl. No.: 671,975

[22] Filed: Jun. 28, 1996

[51] Int. Cl.⁶ .............................. C12Q 1/68; C12P 19/34; C07H 21/04
[52] U.S. Cl. .............................. 435/6; 435/91.2; 435/91.5; 435/91.51; 536/23.5; 536/24.3; 536/24.33; 935/6; 935/8; 935/17; 935/77; 935/78
[58] Field of Search .................................. 536/23.1, 24.3, 536/24.33, 23.5; 436/6, 91.2, 91.51; 935/6, 8, 77, 78, 17; 435/91.5

[56] References Cited

PUBLICATIONS

"Frequent Loss of Heterozygosity of the Long Arm of Chromosome 7 . . . ", Kuniyasu, et al. *Int. J. of Cancer*, 59, (Jul. 1994), pp. 597–600.

"Loss of Heterozygosity in Human Primary Prostate Carcinomas . . . ", Zenklusen, et al., *Cancer Research*, 54, (Dec. 1994), pp. 6370–6373.

"Frequent Loss of Heterozygosity in Human Primary Squamous Cell and Colon Carcinomas . . . ", Zenklusen, et al., *Cancer Research*, (Mar. 1995), pp. 1347–1350.

"Chromosome 7q Allelic Losses in Pancreatic Carcinoma", by Achille, et al., *Cancer Research*, (Aug. 1996), pp. 3808–3813.

"Location of Genes Involved in Invasion and Metastasis on Human Chromosome 7", by Collard, et al., *Cancer Research*, (Dec. 1987), pp. 6666–6670.

"A Factor Encoded by 7q31 Suppresses Expansion of the 7q–Clone and Delays Cytogenetic Progression", by Pedersen, et al., *Cancer Genet Cytogenet*, 78 (1994), pp. 181–188.

"Loss of Heterozygosity on chromosome 7q and aggressive primary breast cancer", by Bieche, et al., *The Lancet*, Jan. 18, 1992, vol. 339, pp. 139–143.

"Allelic loss at 7q31.1 in human primary ovarian carcinomas suggests the existence of a tumor suppressor gene", by Zenklusen, et al., *Oncogene*, vol. 11, No. 1, Jul. 6, 1995, pp. 359–363.

"Frequent Loss of Heterozygosity at 7q31.1 in Primary Prostate Cancer is Associated with Tumor Aggressiveness and Progression", by Takahashi, et al., *Cancer Research*, 55, (Sep. 1995), pp. 4114–4119.

(List continued on next page.)

*Primary Examiner*—Carla J. Myers
*Assistant Examiner*—Debra Shoemaker
*Attorney, Agent, or Firm*—Calfee, Halter & Griswold LLP

[57] ABSTRACT

The present invention provides a novel method for detecting the presence, or absence, or reduced level of an mRNA transcript of a novel tumor suppressor gene, hereinafter referred to as the "CATR1 gene". The method comprises isolating mRNA from tissue samples, amplifying the mRNA by reverse transcriptase-PCR using primers specific to a region in the CATR1 gene, and detecting the presence or absence of the amplified product to determine whether CATR1 mRNA is present or absent or present at reduced levels in the tissue sample. Optionally, the CATR1 mRNA when present, is also quantified. The present invention also relates to the primers which are used in the method. The present invention also relates to a segment of the CATR1 gene, hereinafter referred to as the "CATR 1.3 genetic element," which is useful for designing the primers used in the method of detecting CATR1 mRNA. The CATR 1.3 genetic element is also useful for preparing antisense nucleic acid segments which are CATR1 gene specific inhibitors.

19 Claims, 4 Drawing Sheets

OTHER PUBLICATIONS

"A molecular mechanism influencing the conversion of chemical carcinogen transformed human cells to a transplantable malignant phenotype", Li, et al., (Abstract 1063), Proceedings of the American Assoc. of Cancer Research, vol. 37, Mar. 1996.

"Identification of Gene(s) Associated with Expression of Tumorigenicity" by Li, et al., Abstract #2020, American Society for Cell Biology, 35th Annual Meeting, Dec. 1995.

"Identification of Novel Genetic Elements Associated with the Progression to a Tumorigenic Phenotype" by Li, et al., Abstract 040, 8th Int. Conf. of Int. Soc of Differentiation (ISD), Oct. 22–26, 1994.

"c–Ha–ras 12 condon mutations in human head and neck malignancies", Gemlick, et al., Abstract 1743, 85th Annual Meeting, Apr. 10–13, 1994, vol. 35.

"Malignant conversion of human cells by antisense cDNA to a putative tumor suppressor gene", by Li, et al., *Carcinogenesis*, vol. 17, No. 8, (1996) pp. 1751–1755.

"Tumor Cell Phenotypes: Morphologic and Molecular Characterizations" by Shuler, et al., *Molecular Biology of Cancer*, vol. 1, 1996, pp. 1–9.

"Non–tumorigenic squamous cell carcinoma line converted to tumorigenicity with methyl methanesulfonate without activation of HRAS or MYC" from the Proc. Nat. Acad. Sci. USA, by Milo et al., vol. 87, Feb. 1990, pp. 1268–1272.

"Plastic Tumor Cell Phenotypes" from the Molecular Biology of Cancer, by Shuler et al., vol. 1, 1996, pp. 1–9.

"Malignant conversion of chemically transformed normal human cells", by Milo, et al., Proc. Natl. Acad. Sci. USA, vol. 93, May 1996, pp. 5229–5234.

"Cloning and sequencing of CATR1.3, a human gene associated with tumorigenic conversion" by Li, et al., Proc. Natl. Acad. Sci. USA, vol. 92, Jul. 1995, pp. 6409–6413.

"Rapid production of full–length cDNAs from rare transcripts: Amplification using a single gene–specific oligonucleotide primer" by Frohman, et al., Proc. Natl. Acad. Sci. USA, vol. 85, Dec. 1988 pp. 8998–9002.

"Race: Rapid Amplification of cDNA Ends" by Michael A. Frohman (Chapter 4 from PCR Protocols: A Guide to Methods and Applications, 1990, pp. 28–38.

Yu et al. Biochem. Biophys. Res. Comm. 192:948–953 (Apr. 1993).

Green et. al. Genomics 25: 170–183 (Jan. 1995).

Wang et. al. in Innis et al. editors PCR Protocols. Academic Press, Inc, New York (1990) pp. 70–75.

Ausubel et al. editors Short Protocols in Molecular Biology. John Wiley & Sons, New York (1989) pp. 185–194.

```
  1 ACCAGCACACCACTGTGTAATTTCTATACGAGGTTTGGCTTGGAT                                                    45

ATG GTG CTA AAT GAA GAG ATT CCT CGA CAT TTG CTT CTC ACT CAA AAT AAT GAC ATA ATT CCG AAG CAC CAT     117
Met Val Leu Asn Glu Glu Ile Pro Arg His Leu Leu Leu Thr Gln Asn Asn Asp Ile Ile Pro Lys His His     24

ATC TTA ATC TTA CCA GCA GTA GAC AGT TAT CAA AAA AGT GTT AAT GAT TTA AGA GCT CTA ACA TTT TCT AGG     189
Ile Leu Ile Leu Pro Ala Val Asp Ser Tyr Gln Lys Ser Val Asn Asp Leu Arg Ala Leu Thr Phe Ser Lys     48

TTT CAA GAA TTA AAG CAT GCC CAT GAA TTA AGA AAC CTT TGT GTC TCC CAA TCA AGG TTT CTA GCT ATT ATG     261
Phe Gln Glu Leu Lys His Ala His Glu Leu Arg Asn Leu Cys Val Ser Gln Ser Arg Phe Leu Ala Ile Met     72

TGG TTT GGG ACT AAC ACC AAC TGA TGATGACAATGCACAAAAAATTCCACCATTCATTCATTATACTAAAGGCTAATTGCATGGGCC     349
Trp Phe Gly Thr Asn Thr Asn Ter  79

TATTATTGGAATATGCTTCCTAGTAGTTCAACTAGCTGCATTCAATAGAGTAAAGAGGGTTTTCTGGAGAAACCCTACTGTGAAAAGATGAACTTT    444
GTCTTAACAACTTTAGTTTCAAAAACTATTCATTTATAGATGCCTATTTCACGTCTCTGAAGCAAAATGGTTCATTGTTATGTAGATTACTAAG     539
CAGTCAGTCACTTAAGAATAAAAGTTTCTTCTTTAGAGGCTCCAGCTAACTGTGTCATAGGTCATAAAACCAGCAAAGCATACTGCTA          634
AATAGATAGCAAATAATTGTTAAACACAAATGAGCACCACCTTCAAATTTCCAAGGCCAATCTAAAGCACCACTTCCAGGCCAATCTATGATTATCCCCAACA 729
AAGACTGGAGCCCCTCTCTCAGAGAAATACAAACACAGGAGAAGAAGAATCATAAAGAACTATGTAATATAAGGAGCAGGAGAAAATGTCA        824
GGTGGGAAAAATGGCCGGAAATGGGAAGAAGAAAACATCCAGGGAGTGACATTCCCCGCCCACTGATACTCCAGAAAAGGTAACACATAT         919
CCCCATCTTAATGACTTCTATAATATAATTGCTCTTATAAAGAGGTTAGAACCCACTAGTCTAAAGCTCTAATCATAGTCTGCTCGTTCCCAGTTATCTTGCA 1014
GCACATATAATGAATGGCTGGCCCCTGCTGTCCCCTTTACTACTTTCAGTTCATTAGGCATAGCAGGTGTCAAATATTAAGTGGCACTAATATCAATTTA    1109
TAATATGAATGGCTGGCCCCTGCTGTCCCCTTTACTACTTTCAGTTCATTAGGCATAGTAGATAGACTGAAGATAGAGATAAGATGTAATATCAATTTA    1204
ACCTTGATTTCATAAAACTTAAAAACTTAAAAACTTAAAAACTTAAAAAGGGGAGAAAAAGAGATAAGATAAGATGTAACAAAGGTCTGTAATAGAAAAGGC 1299
TGCAGCA 1306
```

*Fig. 1*

CATRALLSEQ 3401BP
TTTTTAGTAGAGGCAGGGTTTCACCATGTTGGCCAGGCTGGTCTCGAACTC
TTGTGAGTCACGCGCCCAGCCCTGAGTAAAGCCAGTATTTAAGAGAAGAGG
AGTTAAGTATTTGTTAGGTTARCATTTAATGTCTGCTTTCAACAAGTATGC
TAGTAAAGTTACTGAAAAAGAAAAAGTTCTTTCAGAATACCGTAACATGGC
GTACTTCAAAAAGTGCAATAAAGCTGGTTGAGAGAAACAAAGAAGTTTCTT
GCTAACTACCTTTGGATGAATTTTCAAGGCAGAGATAAAATCTCCAATGTG
TGGGACAGACCAAACCTTCAGTCTCTACGTCAATGGTACAACAGAGTACTA
TTAAAGGTTTATCATCATCAAAAGCCATTTATTAGGGGGTGTTCTTGTTTT
TTTACAACTTTGTTGGGTAAGATCAAATGACTCCAAAAAACACCTCTGGAA
TCGGGATGCAGAAGTAATCAGTAAAGCCTGGATCGTGTAAGAAAATGGGGC
AAGGAATATCATAGGCAGGGTACAGCTGACAGCAAAGGCACAGATGCAGCA
CCGGGTTGTGGTAGATAAAAGCAGATAAGTAGACAAAAAGCAAGACGGTAG
TGAAGGCTTTATGCCGAGGTAGATGACGGATGCAAAGCACAATTTTAGGAA
CGAGGTATACATGTGTCAAAACTCATCAAATGTATACACTTAAAATTGCTG
AGGACAAAGATAAAGACAAGAATAAGCAGATTATTAAAATACAGGCTGGAA
CCAGCTGATTATACACTTTTTTCCCAACTTCAGCAACATAACACTAGTAGC
AAATCAGGGCTTTATCCCCCCCCCAGGGTGGTTGTTCAATATTCACCAGCA
AGAGTTCCTCGACATTTCTTCTCACRCAAAATAATGACATAATTCCGAAGC
TTAAGAGTCTAACATTTTACTAGTTTCAAGAATTAAAGCATGCCCATGAAT
ACTAACACCAACTGATGATGACAATGCACAAAAAATTCCACCATTCATTCC
TTCAACTAGCTGCATTTCAATAGAGTAAAGAGGGTTTTCTGGAGAAACCCT
TTTATAGATGCCTATTTCACGTCTCTGAAGCAAAATGGTTCATTTGTTATG
CTCCAGCTAACTGTCTGCATAGGTTCAATCTAAAAACCAGCAAAGCATACT
ATTTTCCAATCCACTTTCCAAGGGCCAATCTATGATTATCCCCAACAAAGA
AAAGAACTATGTAATATAAGGA

MATCH TO FIG. 2B

CATR-FOR
<u>GCAGGGAGAAAATGTCAGG</u>TGGGAAAAATGGCCGGAAATGGGAAGAAGAAA
AGATTGATTCCCCATCTTAATGACTTCTATAATATAATCTCAAGAAAATTC
TGCACATATAAATAATGAATTTGCTCTTATAAAGAGGTTAGAACCCACTAG
AATGGCTGGCCCCTGCTGCTCCCTTTACTACTTCAAGTT<u>CATTAGGCATAG</u>
CATR-REV

AAATATTAAGTGGCACTAATATCAATTTAACATTGATTTCATAAAACTTAA
AGAAATAAAGTAACAGGTTCAAAATTACTGTCAAGGTTTTATTCTGAAAAA
CAGAGAACTCTGCGTTCCAAAACAAATGAATATGGCTTTATTCAACTGGGC
GTTGGAAGTTTGATAAAACTTGTATAAACAGTGTTTAAAAAAATCAAAAA
AAAACTATACAGAAGTGTAGTTAACAGGAAAATACCTTATTTGATAATAC
GGATGAAAGAAGTGGGATAAAAAA

*Fig. 2A*

```
CTGGCCTCATGTGATCCACCCACATCAGCCTCCCAAAGTGCTGGGATTACAG
AACCTACAAGGTATCCTGAGAAACAGATAGATAGGCATCTAGAATTAAGTTA
AATGTCTTACAGAGAAAATTCAAGTTTTAAAAAGAAAAAAAAAATTTGCTTA
TTCCTGGGACAGGAAGGAAACCAATGAGATACACCCTCCTGACCTCTTACCA
TGGAGACCTACTTTAAACGCTTAATCCGTGCCAAAAGTCCAAAGTCCACGAA
CACTTTAATGACTAATACTAGTTTTGAGAGACATTACTACACATCTATGCTC
TTCTCCCCAGTAGTGTTACTGAATTTGCGACTCACTGAGTTGGAAGAGCTGC
TTTTTGAGCAAAGTGCTAGAAACTCCGTTGTACGTTTCCTACCCCATCATAG
TTTCAATACAAGTTGCGATAGTTAAGTGCCAAAACAAGCGGTATGACAGCTG
TTGAGCCAGACTTTAAGGAAAGGCCAAGCAGTCAAGAAGGAATATGATGTCC
ACTGTGCCTAGAACCAGTTGATCAGTTTTATTGCAATAAGAGGTTCATGTAG
AGAGCCAGACCACAGCATTTTGTACTTTATCCTATGAACAGTACATAGCCAG
AATTAATCTGGCAACTGTGTATAGAAAGGTTAATGGAATATCATCATTGTGG
AATTTACTGCATATAAATTATACCTCAGGAAGACCAATTTTTTCAAAACAA
AAAAAGTCAGGCTGTAAAATCCTGAATATTTGATAGCTGAGATTAATTCAAG
CTGAGACCAGCCATGATAGAGTATTTATACCTCAGAAATCAGCAAACATTAC
CACCACTGTGTAATTTCTATACGAGGTTTGGCTTGGATATGGTGCTAAATGA
ACCATATCTTAATCTTACCAGCAGTAGACAGTTATCAAAAAAGTGTTAAGAT
AAGAAACCTTTGTGTCTCCCAATCAAGGTTTCTAGCTATTATGTGGTTTGGG
ATTATACTAAAGGCTAATTGCATGGGCCTATTATTGGAATATGCTTTCCTAG
ACTGTGAAAAGATGAACTTTGTCTTAACAACTTTAGTTTCAAAAACTATTCA
TAGATTACTAAGCAGTCAGTCACTTAAGAATAAAAAGTTTCTTCTTTAGAGG
GCTAAATATGATAGCAAATAATTGTTTAAACACAAATGAGCACCACCTTCAA
CTGGAGCCCCTCTCTCTCAGAGAAGGAATACAAAACACAGGAGAAAGATCAT

CATGTACAAGAATCACCAGGAGAGTGACATTCCCCGCCCCACTGATACCTAG
TTGAAACTCAAATACCTATAAATCCAGAGGAAAAAGGAAAAGGTAACACATA
TCTAAAGCTCTAATCATAGTCTGCTCGTTCTCCAGTTATCTTGCATAATATG
CAGGTGTC

AAAGGGGAAGAGAATACTATACTTCGGCCTTTTTAAAGCAATACATGCAAAA
AGCAAAACTACAGATGGATACACTAGACAGAATGCTAAATGCAATCTACATG
CCAGTTTCCATTGTCCCTTTGGAAGATTTATGAGAGGCAGTACCCATTATCT
GTAATCTAAAGAGATATAGAAAAATAGTGTCTTCTTGATTGAAATTCTGCTT
GTTCAAATAGCTATTATTAGCTGCCTGTATTTATTATCTTTATCAACATTTA
```

Fig. 2B

DETECTING THE EXPRESSION OF THE CATR1 GENE IN SQUAMOUS CELL CARCINOMA

BACKGROUND OF THE INVENTION

Typically, squamous cell carcinomas of the head and neck and tissues adjacent to the tumor tissue are characterized by a morphological examination of the tissues. Typically, the morphological examination involves the sectioning and staining of an excised tissue sample followed by microscopic examination by a cytologist or pathologist. However, current techniques provide no molecular information about the tumor or the surrounding tissue. Thus, the diagnosis, prognosis, monitoring of efficacy of surgery and therapy all depend upon a visual examination of the morphological characteristics of the tissue.

Accordingly, it is desirable to have a technique to provide additional information, particularly at a molecular level, about the squamous cell carcinoma and adjacent tissue.

SUMMARY OF THE INVENTION

The present invention provides a novel method for detecting the presence, or absence, or reduced level of an mRNA transcript of a novel tumor suppressor gene, hereinafter referred to as the "CATR1 gene". The method comprises isolating mRNA from tissue samples, amplifying the mRNA by reverse transcriptase-PCR using primers specific to a region in the CATR1 gene, and detecting the presence or absence of the amplified product to determine whether CATR1 mRNA is present or absent or present at reduced levels in the tissue sample. Optionally, the CATR1 mRNA when present, is also quantified.

The present invention also relates to the primers which are used in the method. The present invention also relates to a segment of the CATR1 gene, hereinafter referred to as the "CATR 1.3 genetic element," which is useful for designing the primers used in the method of detecting CATR1 mRNA. The CATR 1.3 genetic element is also useful for preparing antisense nucleic acid segments which are CATR1 gene specific inhibitors.

BRIEF DESCRIPTION OF THE DRAWINGS

The file of this patent contains at least one photograph. Copies of this patent with photographs will be provided by the Patent and Trademark Office upon request and payment of the necessary fee.

FIG. 1 is the nucleotide sequence of the CATR 1.3 genetic element, SEQ.ID.NO. 1, with the predicted amino acid sequence of the peptide, SEQ. ID. NO. 3 encoded by a portion of the CATR1 gene, SEQ. ID. NO. 2 listed below the nucleotide sequence.

FIGS. 2A and 2B are the nucleotide sequence of the CATR1 gene, SEQ.ID.NO.4, comprising the CATR 1.3 genetic element, an 0.5 kb fragment downstream from the 3' end of the CATR 1.3 genetic element and a 1.6 kb fragment upstream from the 5' end of the CATR 1.3 genetic element.

DETAILED DESCRIPTION OF THE INVENTION

Figure 3:
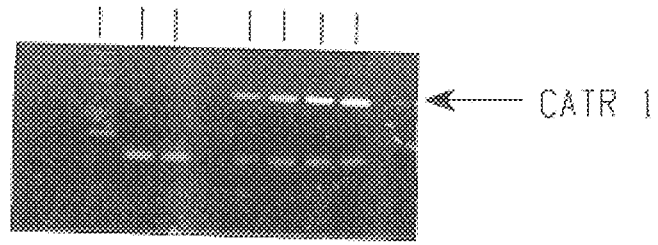
FIG. 3 is a photograph of an agarose gel containing the RT-PCR amplification products of mRNA from tissue samples taken from individuals who do not have squamous cell carcinoma.

A novel tumor suppressor gene has been discovered which is expressed in significant levels in tissue samples derived from healthy individuals, i.e. individuals who do not have squamous cell carcinoma. However, in tumor tissue samples taken from patients with squamous cell carcinoma, particularly of the head and neck, the expression of the normal CATR1 gene in tumor tissue is absent or significantly reduced. It has also been discovered that, in some cases, the levels of CATR1 mRNA are also reduced in the tissue samples taken from areas adjacent to the tumor even though these tissues visually appear to be normal.

The present invention provides a novel method for detecting the presence or absence or reduced levels of an mRNA transcript of a novel tumor suppressor gene, the CATR1 gene. The method comprises isolating mRNA from tissue samples, amplifying the mRNA by a reverse transcriptase-PCR procedure using primers specific to a region in the CATR1 gene, and detecting the presence of the amplified product to determine whether CATR1 mRNA is present or absent or present at reduced levels. Optionally, the CATR1 mRNA present is also quantified.

The present invention also relates to the primers which are used in the method and also to a component of the CATR1 gene, hereinafter referred to as the "CATR 1.3 genetic element". The CATR 1.3 genetic element is useful for designing the primers used in the method of detecting CATR1 mRNA. The CATR 1.3 genetic element is also useful for preparing antisense nucleic acid segments which are CATR1 gene specific inhibitors.

Cloning and Sequencing of the CATR 1.3 Genetic Element

The SCC-83-01-82 cell line, which was derived from a poorly differentiated invasive squamous cell carcinoma, lacks the capacity to produce tumors when transplanted into nude mice. Milo et al. (1990), PNAS 87: 1268–1272. The SCC 83-01-82 cell line was treated with the chemical carcinogen, methyl methanesulfonate to produce a cell which is tumorigenic when transplanted into nude mice. Cells from these tumors are designated "SCC-83-01-82 CA". A cDNA library was constructed using total RNA isolated from the SCC-83-01-82CA cells using the cDNA library construction kit from Invitrogen according to manufacturer's instructions.

Poly(A)$^+$ RNA was selected from the total RNA obtained from the SCC-83-01-82CA cells using the FastTrack mRNA kit from Invitrogen according to the manufacturer's instructions. Five micrograms of poly(A)$^+$ RNA was used to synthesize first strand cDNA, using oligo (dT) primers and Superscript reverse transcriptase from GIBCO/BRL. Then the BstXI cloning linkers, 5'-GAATTCCACCACA, SEQ.ID.NO. 17 and 5'-GTGGAATTC, SEQ.ID.NO. 6 were added to both ends of oligo (dT)-primed cDNA. The cDNA with linkers was then purified using a cDNA spin column from Pharmacia and then ligated to the BstXI site of the eukaryotic expression vector pRC/RSV from Invitrogen. The ligation mixture was used to transform *Escherichia coli* strain DHIOB. The cDNA library was plated out on Luria-Bertani plates containing ampicillin at 50 µg/ml. Then 1.1×10$^6$ colonies from primary plates were pooled in 200 ml of Luria-Bertani medium containing 7% (vol/vol) dimethyl sulfoxide and stored at minus 20° C. as library stock.

Plasmid DNA was purified from the cDNA library stock as follows: 10 ml of the cDNA library stock was seeded into 500 ml of terrific broth medium containing ampicillin, and incubated at 37° C. overnight with shaking. Supercoiled plasmid DNA was isolated from the stock by CsCl gradient ultracentrifugation as described in Radloff et al., *Proc. Natl.*

Acad. Sci. USA 57: 1514–1521 (1967) and used to transfect the nontumorigenic squamous cell carcinoma cell line SCC-83-01-82. For each batch of transfection, eight 15-cm plates of the non-tumorigenic cells, grown in Minimal Essential Medium containing 10% fetal bovine serum, at 60% confluency were used. The plates were washed twice with 20 ml of phosphate-buffered saline. Then 40 µl of LipofectAce from GIBCO/BRL and 30 µg of Sal I linearized plasmid in 5 ml of serum-free medium were added to each plate. After overnight incubation, 5 ml of fresh medium containing 20% fetal bovine serum was added. The plates were incubated for another 24 hours. The medium was then replaced by 20 ml of fresh Minimal Essential Medium containing 10% fetal bovine serum. G418 from GIBCO/BRL was added at 250 µg/ml for the selection of pRC/RSV-transfected cells. After 2 days, the cell cultures were split 1 to 4 in Modified Eagle Medium with 10% fetal bovine serum and G418 at 250 µg/ml, and after 2 weeks the G418-resistant colonies were pooled. Cells from the G418-resistant colonies were grown in Minimal Essential Medium 10% fetal bovine serum to generate greater than $10^7$ transfected cells and to produce the transfected cell line, designated as SCC-83-01-82CATRI. Then 18 nude mice were injected subcutaneously with approximately $10^7$ of the transfected SCC-83-01-82 CATRI cells. Three of the injected mice developed progressively growing tumors that exhibited a histology consistent with a poorly differentiated carcinoma.

Poly(A)$^+$ RNA was isolated from the transfected cell line SCC-83-01-82CATR1 and examined by Northern analysis using a radiolabeled cloning vector as a probe. A 1.5 kb fragment, which represents an 1.3 kb cDNA insert with about 0.2 kb of flanking vector sequence, was detected.

Reverse Transcription (RT)-PCR amplification of the 1.5 kb fragment was carried out on a standard thermal cycler according to the instructions described in the GeneAmp RNA PCR kit obtained from Perkin-Elmer/Cetus. An 0.5 µg sample of total RNA from the SCC-83-01-82 CATR1 cells and the vector downstream primer RS2, were used in the reverse transcription reaction to produce the first strand cDNA. One-fourth of the reverse transcription reaction mixture was then used for PCR amplification with the cloning linker specific primer, 5'-GCCAGTGTGGTGGAATTC, SEQ.ID.NO. 7. The amplification cycle protocol was as follows: 95° C. for 2 minutes, 95° C. for 1 minute, 56° C. for 1 minute, and 72° C. for 2 minutes, through 35 cycles.

The reverse transcriptase product, designated the "CATR 1.3 genetic element" was cloned using the PCRScript cloning kit from Stratagene according to the manufacturer's instructions.

Several clones were selected for sequencing for the purpose of sequence verification. Double-stranded plasmid bearing CATR 1.3 CDNA was sequenced by using USB Sequenase from United States Biochemical. As shown in FIG. 1, the cDNA of the CATR 1.3 genetic element, SEQ.ID.NO. 1 is 1306 base pairs in length. The CATR 1.3 genetic element exhibits a long 3' untranslated region and encodes a peptide, SEQ.ID.NO. 3, of 79 amino acids.

Cloning and Sequencing of the CATR1 Gene

RT-PCR and primers specific to the CATR 1.3 genetic element were used to clone the regions of the CATR1 gene downstream and upstream of the CATR 1.3 genetic element. The template for the reverse transcription reaction was total RNA isolated from normal human fibroblasts.

The 3' end of the CATR1 gene was amplified by RT-PCR using the Marathon cDNA amplification kit from CloneTech according to manufacturer's instructions. In this method first strand cDNA molecules are synthesized using a lock-docking oligo (dT) cDNA primer provided with the kit. Following destruction of the original mRNA template with RNase H and formation of double-stranded cDNA molecules with DNA polymerase I and DNA ligase, an adaptor provided with the kit is ligated to both ends of the cDNA molecules to provide a library of cDNAs. The 3' end of the adaptor ligated cDNA is amplified using an adaptor specific primer provided with the kit and the gene specific primer 15-7: 5'-GCTGCTCCCTTTACTACTTCAAGTT, SEQ.ID.NO. 8. The cycling protocol for the first PCR was as follows: 94° C. centigrade for 30 seconds; 68° C. for 3 minutes for 45 cycles, then at 72° C. for 10 minutes for extension. The cycles ended with 4° C. soak.

After the first PCR, a 100 times dilution of the first PCR product was made. 2 microliters of the diluted DNA was taken for second round of PCR. A secondary PCR was performed as follows: 94° C. for 30 seconds; 68° C. for 3 minutes for 40 cycles, then at 72° C. for 10 minutes for extension. The cycles ended with 4° C. soak.

The region of the CATR1 gene upstream of the CATR 1.3 genetic element was amplified using a polymerase chain reaction kit available under the trade name 5' RACE from BRL/GIBCO according to the manufacture's instructions. This method uses a gene specific primer (GSP1) for reverse transcription of the template RNA. After first strand cDNA synthesis, the original mRNA template is destroyed with RNase H, and a homopolymer dC tail is appended to the 5' end of the first-strand reaction products using terminal transferase. Amplification is accomplished using Taq DNA polymerase. The antisense gene specific primer (GSP2) used in the amplification anneals to a internal site in the cDNA molecule upstream of the sequence encoding GSPI. The sense primer is a deoxyinosine-containing anchor primer provided with the system.

Multiple rounds of amplification were performed in which the nested gene-specific primer used in a subsequent round annealed to a site in the cDNA molecule upstream of the nested-gene-specific primer used in the previous round.

For 5' RACE PCR two primers were used, one primer, a Universal Amplification Primer-UAP provided with the kit, and one a gene specific primer, which anneals to a region in CATR 1.3, designated 1.3R1 and having the sequence 5'-GAAGCAAATGTCGAGGAATCTC; SEQ. ID. NO. 9. The cycling protocol for the first PCR was as follows: 90° C. for one minute; 57° C. for 30 seconds; and 72° C. for two minutes for 35 cycles. The cycling protocol for the second round of PCR was as follows: 90° C. for one minute; 55° C. for 30 seconds; 72° C. for two minutes for 25 cycles, then at 72° C. for 10 minutes for extension. The cycles ended with 4° C. soak.

Nucleotide Sequence of the Human CATR1 Gene

The nucleotide sequence of the CATR1 gene, SEQ.ID.NO. 4 is shown in FIG. 2 comprising encompassing the 1.6, 1.3, and 0.5 regions. The CATRI gene comprises 3401 base pairs. Examination of the metaphase chromosomes from normal human foreskin cells using digoxigenin-labeled CATR 1.3 genetic element as a probe, established the location of the CATR1 gene on the q arm of chromosome 7 at band 31-32. This site has been shown to be involved in prostate, breast, lymphoid, and myeloid human cancers as well as head and neck cancers.

Method of Determining CATR mRNA Levels in Tissue Samples

The CATR 1.3 genetic element is useful for designing probes that are used in a method for measuring CATR1 mRNA levels in tissue samples from patients preferably with squamous cell carcinomas of the head and neck.

Preferably, the CATR mRNA levels in one or more tissue samples from the noninvolved area adjoining or preferably distal to the tumor site are also determined. Preferably, all tissue samples are snap-frozen in liquid nitrogen immediately following resection.

RNA is isolated from a tissue sample by conventional techniques such as a TRIzol extraction procedure and the presence of CATR1 mRNA is detected by RT-PCR technology using a forward primer that anneals to a region on the antisense strand of the CATR 1 gene and reverse primer which anneal to a region on the sense strand of the CATR 1 gene. Preferably the forward and reverse primers are complementary to regions on the CATR 1.3 genetic element. Preferably, the forward and reverse primers anneal to regions of the CATR1 gene which are separated by between 200 to 600 base pairs, more preferably 300 to 400 base pairs. Preferably, the primers comprise 18–30 nucleotides, more preferably 19–25 nucleotides. Preferably, the primers have a G+C content of 40% or greater. More preferably the forward and reverse primers comprise the following sequences, respectively:

CATR1 sense, 5'-GCAGGGAGAAAATGTCAGG-3;
SEQ.ID.NO. 5

CATR1 antisense, 5'-GACACCTGCTATGCCTAATG-3';
SEQ.ID.NO. 15

Optionally a normalization standard, such as a housekeeping gene, is included in the PCR reaction. The expression of the preferred housekeeping gene is the same level in normal squamous cells and in cells derived from squamous cell carcinoma tumor tissue. Suitable housekeeping genes include, for example, HPRT, or genes encoding actin or tubulin. Primers to the normalization standard are selected such that the length of the PCR amplification product of the normalization standard will vary from the length of the PCR amplification product of CATR1 mRNA to allow separation of the two PCR amplification products on an agarose gel.

Preferably, an internal standard comprising a double-stranded nucleic acid fragment which competes with the CATR 1 gene for the primers is added to the PCR reaction mixture. Preferably, the PCR product that results from amplification of the internal standard is of a different size from that of the PCR product that results from amplification of the CATR1 mRNA to enable separation on an agarose gel.

Preferably, the amplification of the mRNA of CATR1 uses the "hot start tube" procedure in which the reactants are kept separate until the reaction tube is heated to a temperature that minimizes mispriming. This involves keeping the essential reagents separate until the PCR reaction mixture has reached 94° C. and is preferably accomplished using the hot start tube procedure which separates the Taq polymerase, $MgCl_2$, and the cDNA sample from the other reagents by a thin film wax barrier. The reaction then takes place when the temperature reaches 94° C. after the wax melts.

Preferably, the presence of the primer-specific PCR product is detected by separating the PCR products on an agarose gel. The presence of the primer-specific product is detected by ethidium bromide staining of the agarose gel. More preferably, the presence of the primer-specific product is detected by adding alpha-$^{32}$P-deoxynucleotide into the PCR reaction mixture and measuring the amount of radiolabeled deoxynucleotide incorporated into the PCR product by gel scanning using autoradiograms, or by liquid scintillation counting of excised portions of the gel.

The following examples, which describe in greater detail the procedures for determining CATR1 gene expression levels in tissue samples, are intended to illustrate but not limit the procedures.

EXAMPLE 1

Reverse transcriptase-polymerase chain reaction amplification, employing primers which anneal to regions in the CATR 1.3 cDNA and to a normalization standard, was used to determine the levels of CATR1 mRNA in tissue samples obtained from the oropharyngeal cavity of twelve patients diagnosed as having squamous cell carcinomas. Specifically, two samples of tissue were taken from each patient. One of the tissue samples was taken from a visually identifiable tumor and was diagnosed as being positive for squamous cell carcinoma by a board certified pathologist. One of the matched samples was visually determined as being noninvolved tissue and was taken from a region at least 4 cm beyond the border of the tumor. The samples were removed from the oropharyngeal cavity of each patient and snap-frozen in liquid nitrogen immediately following resection.

Then 100–150 mg of each frozen tissue sample was homogenized in 1.0–1.5 ml TRIzol reagent obtained from Life Technologies, using an Ultra-Turrax homogenizer. Following the addition of 0.3 ml chloroform and centrifugation, the aqueous phase was re-extracted with TRlzol reagent to eliminate contaminating DNA. RNA was precipitated from the resulting aqueous phase with isopropyl alcohol and washed with 75% ethanol. The concentration of RNA was determined spectrophotometrically after dissolving in DEPC water.

Then 2 µg of RNA was dissolved in DEPC water with reverse transcription performed for 60 minutes at 37° C. in a volume of 20 µl. The reaction mixture contained 1× PCR buffer from GIBCO/BRL, 5 mM $MgCl_2$, 100 pmoles random hexamers, 1 unit/µl RNASin, 1 mM each of dATP, dGTP, dCTP, and dTTP, and 100 units of Superscript II reverse transcriptase. After completion of the reverse transcription reaction, the samples were preincubated at room temperature for 10 minutes and heated to 99° C. for 5 minutes to terminate the reaction. Approximately 200 ng of cDNA from each sample was amplified using sense and antisense primers for either HPRT or CATR1 in separate reactions.

All pre-PCR mixtures contained 1× PCR buffer, 1.5 mM $MgCl_2$, 0.25 µM each of sense and antisense primer for either HPRT or CATRI, 0.2 mM each of dATP, dGTP, dCTP, and dTTP, (0.5 µl of alpha-$^{32}$P-dCTP, at 3000 Ci/mmol, from NEN Research Products, 550 ng Taq Start Antibody and 2.5 units of Taq DNA polymerase in a final volume of 50 µl.

Hypoxanthine phosphoribosyl transferase hereinafter referred to as "HPRT" was used as a standard control for PCR amplification. The primer set for amplification of HPRT was HRPT sense primer 5'-GTAAGACCAGTCAACAGGGGAC-3', SEQ.ID.NO. 18 HPRT antisense, 5'-CCAGCAAGCTTGC-GACCTTGACCA-3', SEQ.ID.NO. 19.

The size of the HPRT PCR product made using these primers is 177 base pairs. The primer set for amplification of CATR1 was; CATR1 Sense, 5'-GCAGGGAGAAAATGTCAGG-3', SEQ.ID.NO. 5; CATR1 antisense, 5'-GACACCTGCTATGCCTAATG-3', SEQ.ID.NO. 15.

Figure 4:
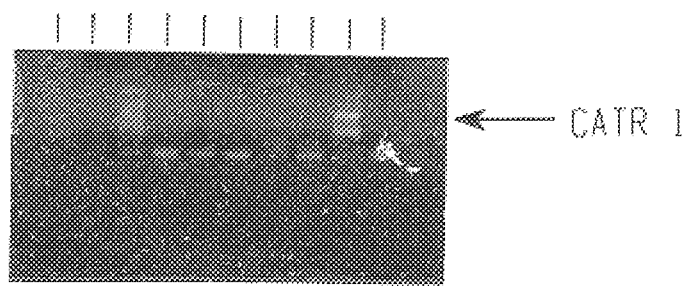
FIG. 4 is a photograph of an agarose gel containing RT-PCR amplification products of mRNA from squamous cell carcinoma tissue samples and from matching tissue samples adjacent to the tumor.

The CATR PCR product formed using these primers comprises 368 base pairs and has the nucleotide sequence of SEQ. ID. NO.20. For CATR1, the reactants were subjected to 35 cycles of amplification under the following conditions: 94° C. for 1 minute, 57° C. for 1 minute, and 68° C. for 1 minute followed by an incubation for 7 minutes at 72° C. A 5 μl aliquot of the CATR1 amplified product from each sample was then reamplified under similar conditions for an additional 10–15 cycles. For HPRT, the reactants were subjected to 28–31 cycles of amplification under the following conditions: 95° C. for 15 seconds, 60° C. for 30 seconds and 72° C. for 30 seconds, followed by an incubation for 7 minutes at 72° C. The PCR amplified products were analyzed by electrophoresis on an 1.8% agarose gel, and quantified by ethidium bromide staining. Representative results are shown in FIG. 4.

COMPARATIVE EXAMPLE

RT-PCR, employing primers which anneal to regions in the CATR 1.3 cDNA and a normalization standard, was also used to determine the levels of CATR1 mRNA in a breast tissue sample obtained from a healthy individual, i.e. an individual who did not exhibit squamous cell carcinoma. The sample was snap-frozen in liquid nitrogen immediately after removal. RNA was extracted from the samples as described above for Example 1 and the mRNA reverse transcribed and amplified as described above for Example 1. The PCR amplified products were separated on an agarose gel and detected with ethidium bromide staining.

As shown in FIG. 3, lanes 4–7, a heavily stained band at the migration position for the CATR1 amplification product was detected in the lanes containing PCR amplification products from the tissues derived from the healthy individual.

As shown in FIG. 4, a band at the migration position for 368 base pairs, which is the predicted size of the CATR1 PCR product, was detected in the lanes 3, 5, 7, and 9. Each of these lanes contains PCR products from a tissue sample taken from a noninvolved area in four of the patients. In contrast, as shown in FIG. 4, no bands at approximately 368 base pairs were detected in the lanes 4, 6, 8 and 10. These lanes contains PCR products from the tumor tissue samples taken from these same four patients. In addition, no CATR1 PCR products were detected on the agarose gels which contained the amplification products for the eight remaining tumor samples or for the samples taken from non-involved areas from the eight remaining patients. Since each of these non-involved samples was taken from an area in close proximity to the tumor tissue, it is believed that the reduction in CATR1 mRNA levels in these samples may be due to a release of gene suppression factors from the nearby tumor. Alternatively, the reduction in mRNA levels in these samples may be a signal that these cells, which appear to be non-involved in the tumor are predisposed to becoming cancerous.

These results show that this method is useful for determining the levels of CATR1 mRNA in tumor tissue and non-involved tissue from individuals with squamous cell carcinoma and for distinguishing squamous cell carcinoma tissue from healthy tissue.

EXAMPLE 2

RT-PCR-amplification, employing primers which anneal to regions in the CATR 1.3 cDNA and an internal standard, is used to quantitate CATR1 gene expression in tissue samples obtained from the oropharyngeal cavity of a patient.

The cDNA in each sample is divided into two unequal aliquots. The smaller amount of cDNA is amplified using sense and antisense primers for HPRT. The housekeeping gene, HPRT, is used as a control for the amount of RNA in each sample. The larger amount of cDNA is divided into 6 aliquots, each containing a constant amount of cDNA. A dilution series of an internal standard is made and a known amount of each added separately to the 6 tubes. The internal standard is 1149 base pairs and comprises sequences which anneal to the CATR1 sense and antisense primers. Water controls and reverse transcriptase minus reactions are run as negative controls.

All pre-PCR mixtures contain IX PCR buffer, 1.5 mM $MgCl_2$, 0.25 μM each of sense and antisense primer for either HPRT or CATRI, 0.2 mM each of dATP, dGTP, dCTP, and dTTP, and 2.5 units of Taq DNA polymerase in a final volume of 50 μl. Preferably, quantification of the primer-specific PCR product is accomplished by adding alpha$^{32}$P-dCTP (0.5 μl of alpha-$^{32}$P dCTP (3000 Ci/mmol) (NEN Research Products), into the PCR reaction mixture and comparing the amount of radiolabeled dCTP incorporated into each of the PCR products by gel scanning.

Amplification uses the hot start tube procedure and conditions as follows for CATR1: 94° C. for 1 minute, 57° C. for 1 minute, and 68° C. for 1 minute followed by an incubation for 7 minutes at 72° C. for 35 cycles. For HPRT, 95° C. for 15 seconds, 60° C. for 30 seconds and 72° C. for 30 seconds, followed by an incubation for 7 minutes at 72° C. for 28–31 cycles.

Specific amplification will be achieved by using the following primer sets: HPRT sense, 5'-GTAATGACCAGTCAACAGGGGAC-3', SEQ.ID.NO. 18; HPRT antisense, 5'-CCAGCAAGCTTGCGACCTTGACCA-3', SEQ.ID.NO. 19; CATR1 Sense, 5'-GCAGGGAGAAAATGTCAGG-3, SEQ.ID.NO. 5; CATR1 antisense, 5'-GACACCTGCTATGCCTAATG-3', SEQ.ID.NO. 15. The amplified product for HPRT is 177 bp; for CATR1 368 bp, for the internal standard 216 base pairs.

All amplified products are analyzed on an 1.8% agarose gel. If no amplified product is detected by visual examination of the gel, 5 μl of the PCR reacted mixture is used for a second round of 13–15 cycles of PCR using the above conditions in Hot start tubes.

For quantification of CATRI expression in a given sample, the amount of products generated by CATRI target (Pt) and the internal standard (Ps) are determined for each individual reaction in the dilution series of six reactions. The log of the molar ratio of Pt/Ps is plotted versus the log of the known molar amount of internal standard competitor added to each reaction.

The initial amount of CATR1 cDNA in the sample, hereinafter referred to as "PTO", is extrapolated from the graph where log Pt/Ps=1/1=0, where the molar ratio of Pt and Ps are equal. Since the CATRI target sequence is longer than the internal standard sequence and therefore incorporates more label, a correction factor of 1.7 is used to calculate Pto. The absolute molar amount of CATRI cDNA in a given sample is normalized to the amount of HPRT product in the HPRT band. The results are reported as; molar amount CATRI cDNA/moles $^{32}$p incorporated HPRT cDNA to provide values for quantifying CATRI mRNA in tissue samples.

The method for determining CATR1 mRNA levels in tissue samples is useful as an aid in diagnosing squamous cell carcinoma and identifying patients at increased risk for tumorigenic spread through direct invasion and metastasis. The method for determining CATR1 mRNA levels in tissue samples is also useful for assessing the effect of squamous cell carcinoma on non-involved tissues. The method for determining CATR1 mRNA levels is also useful for determining the efficacy of treatments for squamous cell carcinoma.

Method of Preparing Antisense CATR1.3 Expression Vector

The CATR 1.3 genetic element was used to prepare sense and antisense CATRI expression vectors by ligating to the BstXI sites of the eukaryotic expression vector pRC/RSV from Invitrogen. Individual clones were verified for either sense or antisense orientation by restriction digestion patterns.

EXAMPLE 3

Converting Nontumorigenic SCC Cells to Tumorigenic Cells with an Antisense CATR 1.3 Expression Vector Nontumorigenic SCC cells were transfected with plasmids containing the CATR 1.3 genetic element in the antisense orientation, hereinafter referred to as the "antisense construct," using Lipofectin from GIBCO/BRL, Gaithersburg, Md., according to manufacturer's instructions. Two 10 cm plates of the nontumorigenic SCC cells grown to 60% confluency were used for transfection with antisense construct. For each dish, 20, µl of Lipofectin and 10, µg of super coiled plasmid were incubated in 0.8 ml Minimal Essential Medium for 20 minutes. 3.2 ml Minimal Essential Medium was then added to the DNA-Lipofectin mixture. The plates were washed twice with Minimal Essential Medium and the diluted DNA-Lipofectin mixture was added to each plate. After overnight incubation, 5 ml fresh medium containing 20% fetal bovine serum was added. The plates were incubated for another 24 hours. The medium was then replaced by 10 ml fresh Modified Eagle Medium containing 10% fetal bovine serum. After 2 days, the cells were split 1:4 in Modified Eagle Medium with 10% fetal bovine serum and 250, µg/ml G418 for selection of stably transfected cells. G418 resistant colonies from both plates per condition were pooled. The cells were then resuspended in Minimal Essential Medium at 2×10$^7$ cells per ml.

COMPARATIVE EXAMPLE

Nontumorigenic SCC cells were transfected with plasmids containing the CATR 1.3 genetic element in the sense orientation, hereinafter referred to as the "sense construct," as described above for example 3 and then resuspended in Minimal Essential Medium at 2×10$^7$ cells per ml.

Three to four week old male gnotobiotic nude mice were splenectomized and then 10$^7$ cells transfected with the sense construct were injected subcutaneously into the flanks of seventeen nude mice and 10$^7$ cells transfected with the antisense construct were injected subcutaneously into the flanks of fifteen nude mice. Progressively growing tumors were produced within at three and one-half months at the injection site in six out of the fifteen nude mice injected with cells transfected with the antisense construct. No tumors were observed within five months in the seventeen mice injected with cells transfected with the sense construct.

The tumors produced by cells transfected with the antisense construct had a histopathology that was consistent with that of the original patient tumor, and with that of tumors produced by SCC-83-01-82 cells treated with methyl methanesulfonate, and with that of tumors produced by SCC-83-01-82 CATRI cells.

Total RNA was isolated from the tumor cells of the progressively growing tumors and used for RT-PCR. Reverse transcription of first cDNA strand was performed using pRC/RSV specific primer, SPT2 AGGAAAGGACAGTGGGAGTG, SEQ.ID.NO. 10, which is located downstream from the insertion site. The cDNA was divided into two aliquots, one for CATR 1.3 sense strand specific amplification and one for CATR 1.3 antisense strand specific amplification.

Primary PCR was performed at 95° C. for 1 minute, 65° C. for 1 minute, 72° C. for 2 minutes, for 35 cycles. For sense strand specific amplification, vector upstream primer RSI CATTCACCACATTGGTGTGCAC, SEQ.ID.NO. 11 and CATRI downstream primer CATR 1.3-2R CAGCCTTTTCTATTACAGACCTTTGTTACATTG, SEQ.ID.NO. 12 were used.

For antisense specific amplification, primers RS1 and CATR1.3-2F CACCACTGTGTAATTTCTATACGAGGTTTGG, SEQ.ID.NO. 13 were used.

Secondary PCR was performed as 95° C. for 1 minute, 50° C. for 1 minute, and 72° C. for 2 minutes, for 30 cycles using a 2 µl reaction mixture from primary PCR. For sense strand amplification, vector upstream primer BEI GGTACCGAGCTCGGATCCACTAGTA, SEQ.ID.NO. 14 and CATRI downstream primer 15-1 GACACCTGCTATGCCTAATG, SEQ.ID.NO. 15 were used. For antisense strand amplification, BE1 and CATR1 downstream primer 15-2 CAAGAATTAAAGCATGCC, SEQ.ID.NO. 16 were used. 10 µl PCR product from each amplification was used for electrophoresis on 1.2% agarose gel containing ethidium bromide. A distinct band of approximately 1.3 kb was observed in the lane containing PCR products amplified with the antisense primers. In contrast, the band at 1.3 kb was absent in the lane containing the PCR products amplified with the sense primers. These results establish that the conversion of the nontumorigenic cells to a tumorigenic stage resulted from expression of the antisense construct of the CATR 1.3 genetic element and not from transfection with the vector. Thus, the antisense construct prepared with the CATR 1.3 genetic element is a CATR1 gene specific inhibitor that is capable of converting nontumorigenic cells from a squamous cell carcinoma into a tumorigenic stage.

In addition to the CATR1 gene and the CATR1.3 genetic element, the present invention also includes: DNA molecules which, but for the degeneracy of the genetic code would hybridize to the sense strand of CATR1 cDNA and to the antisense strand of CATR1 cDNA; DNA molecules having the sequences shown in FIGS. 1 and 2 and DNA molecules having sequences complementary thereto; heterologous DNA having substantial sequence homology to the DNA sequences in FIGS. 1 and 2 or portions thereof.

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
        ( A ) LENGTH: 1306 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: mat_peptide
        ( B ) LOCATION: 46..87

( x i ) SEQUENCE DESCRIPTION: SEQ ID NO:1:

```
ACCAGCACAC  CACTGTGTAA  TTTCTATACG  AGGTTTGGCT  TGGATATGGT  GCTAAATGAA    60
GAGATTCCTC  GACATTTGCT  TCTCACTCAA  AATAATGACA  TAATTCCGAA  GCACCATATC   120
TTAATCTTAC  CAGCAGTAGA  CAGTTATCAA  AAAAGTGTTA  ATGATTTAAG  AGCTCTAACA   180
TTTTCTAAGT  TTCAAGAATT  AAAGCATGCC  CATGAATTAA  GAAACCTTTG  TGTCTCCAA    240
TCAAGGTTTC  TAGCTATTAT  GTGGTTTGGG  ACTAACACCA  ACTGATGATG  ACAATGCACA   300
AAAAATTCCA  CCATTCATTC  CATTATACTA  AAGGCTAATT  GCATGGGCCT  ATTATTGGAA   360
TATGCTTTCC  TAGTTCAACT  AGCTGCATTT  CAATAGAGTA  AAGAGGGTTT  TCTGGAGAAA   420
CCCTACTGTG  AAAAGATGAA  CTTTGTCTTA  ACAACTTTAG  TTTCAAAAAC  TATTCATTTA   480
TAGATGCCTA  TTTCACGTCT  CTGAAGCAAA  ATGGTTCATT  TGTTATGTAG  ATTACTAAGC   540
AGTCAGTCAC  TTAAGAATAA  AAAGTTTCTT  CTTTAGAGGC  TCCAGCTAAC  TGTCTGCATA   600
GGTTCAATCT  AAAAACCAGC  AAAGCATACT  GCTAAATATG  ATAGCAAATA  ATTGTTTAAA   660
CACAAATGAG  CACCACCTTC  AAATTTTCCA  ATCCACTTTC  CAAGGGCCAA  TCTATGATTA   720
TCCCCAACAA  AGACTGGAGC  CCCTCTCTCT  CAGAGAAGGA  ATACAAAACA  CAGGAGAAAG   780
ATCATAAAGA  ACTATGTAAT  ATAAGGAGCA  GGGAGAAAAT  GTCAGGTGGG  AAAAATGGCC   840
GGAAATGGGA  AGAAGAAACA  TGTACAAGAA  TCACCAGGAG  AGTGACATTC  CCCGCCCAC    900
TGATACCTAG  AGATTGATTC  CCCATCTTAA  TGACTTCTAT  AATATAATCT  CAAGAAAATT   960
CTTGAAACTC  AAATACCTAT  AAATCCAGAG  GAAAAAGGAA  AAGGTAACAC  ATATGCACAT  1020
ATAAATAATG  AATTTGCTCT  TATAAAGAGG  TTAGAACCCA  CTAGTCTAAA  GCTCTAATCA  1080
TAGTCTGCTC  GTTCTCCAGT  TATCTTGCAT  AATATGAATG  GCTGGCCCCT  GCTGCTCCCT  1140
TTACTACTTC  AAGTTCATTA  GGCATAGCAG  GTGTCAAATA  TTAAGTGGCA  CTAATATCAA  1200
TTTAACCTTG  ATTTCATAAA  ACTTAAAAAG  GGGAGAAAAA  GAGATAAAGA  TGTAAGTAGA  1260
TAGACTGACA  ATGTAACAAA  GGTCTGTAAT  AGAAAGGCT   GCAGCA               1306
```

( 2 ) INFORMATION FOR SEQ ID NO:2:

( i ) SEQUENCE CHARACTERISTICS:
        ( A ) LENGTH: 240 base pairs
        ( B ) TYPE: nucleic acid (C) STRANDEDNESS: double
(D) TOPOLOGY: linear (i i) MOLECULE TYPE: cDNA (i x) FEATURE:
 (A) NAME/KEY: CDS
 (B) LOCATION: 1..240

(x i) SEQUENCE DESCRIPTION: SEQ ID NO:2:

| ATG | GTG | CTA | AAT | GAA | GAG | ATT | CCT | CGA | CAT | TTG | CTT | CTC | ACT | CAA | AAT | 48 |
| Met | Val | Leu | Asn | Glu | Glu | Ile | Pro | Arg | His | Leu | Leu | Leu | Thr | Gln | Asn | |
| 1 | | | | 5 | | | | | 10 | | | | | 15 | | |

| AAT | GAC | ATA | ATT | CCG | AAG | CAC | CAT | ATC | TTA | ATC | TTA | CCA | GCA | GTA | GAC | 96 |
| Asn | Asp | Ile | Ile | Pro | Lys | His | His | Ile | Leu | Ile | Leu | Pro | Ala | Val | Asp | |
| | | | 20 | | | | | 25 | | | | | 30 | | | |

| AGT | TAT | CAA | AAA | AGT | GTT | AAT | GAT | TTA | AGA | GCT | CTA | ACA | TTT | TCT | AAG | 144 |
| Ser | Tyr | Gln | Lys | Ser | Val | Asn | Asp | Leu | Arg | Ala | Leu | Thr | Phe | Ser | Lys | |
| | | | 35 | | | | | 40 | | | | | 45 | | | |

| TTT | CAA | GAA | TTA | AAG | CAT | GCC | CAT | GAA | TTA | AGA | AAC | CTT | TGT | GTC | TCC | 192 |
| Phe | Gln | Glu | Leu | Lys | His | Ala | His | Glu | Leu | Arg | Asn | Leu | Cys | Val | Ser | |
| | 50 | | | | | 55 | | | | | 60 | | | | | |

| CAA | TCA | AGG | TTT | CTA | GCT | ATT | ATG | TGG | TTT | GGG | ACT | AAC | ACC | AAC | TGA | 240 |
| Gln | Ser | Arg | Phe | Leu | Ala | Ile | Met | Trp | Phe | Gly | Thr | Asn | Thr | Asn | * | |
| 65 | | | | | 70 | | | | | 75 | | | | | 80 | |

(2) INFORMATION FOR SEQ ID NO:3:

(i) SEQUENCE CHARACTERISTICS:
  (A) LENGTH: 79 amino acids
  (B) TYPE: amino acid
  (D) TOPOLOGY: linear (i i) MOLECULE TYPE: protein (x i) SEQUENCE DESCRIPTION: SEQ ID NO:3:

| Met | Val | Leu | Asn | Glu | Glu | Ile | Pro | Arg | His | Leu | Leu | Leu | Thr | Gln | Asn |
| 1 | | | | 5 | | | | | 10 | | | | | 15 | |

| Asn | Asp | Ile | Ile | Pro | Lys | His | His | Ile | Leu | Ile | Leu | Pro | Ala | Val | Asp |
| | | | 20 | | | | | 25 | | | | | 30 | | |

| Ser | Tyr | Gln | Lys | Ser | Val | Asn | Asp | Leu | Arg | Ala | Leu | Thr | Phe | Ser | Lys |
| | | | 35 | | | | | 40 | | | | | 45 | | |

| Phe | Gln | Glu | Leu | Lys | His | Ala | His | Glu | Leu | Arg | Asn | Leu | Cys | Val | Ser |
| | 50 | | | | | 55 | | | | | 60 | | | | |

| Gln | Ser | Arg | Phe | Leu | Ala | Ile | Met | Trp | Phe | Gly | Thr | Asn | Thr | Asn | |
| 65 | | | | | 70 | | | | | 75 | | | | | 80 |

(2) INFORMATION FOR SEQ ID NO:4:

(i) SEQUENCE CHARACTERISTICS:
  (A) LENGTH: 3401 base pairs
  (B) TYPE: nucleic acid
  (C) STRANDEDNESS: double
  (D) TOPOLOGY: linear (i i) MOLECULE TYPE: cDNA (x i) SEQUENCE DESCRIPTION: SEQ ID NO:4:

| TTTTTAGTAG | AGGCAGGGTT | TCACCATGTT | GGCCAGGCTG | GTCTCGAACT | CCTGGCCTCA | 60 |
| TGTGATCCAC | CCACATCAGC | CTCCCAAAGT | GCTGGGATTA | CAGTTGTGAG | TCACGCGCCC | 120 |
| AGCCCTGAGT | AAAGCCAGTA | TTTAAGAGAA | GAGGAACCTA | CAAGGTATCC | TGAGAAACAG | 180 |
| ATAGATAGGC | ATCTAGAATT | AAGTTAAGTT | AAGTATTTGT | TAGGTTATCA | TTTAATGTCT | 240 |
| GCTTTCAACA | AGTATGCAAT | GTCTTACAGA | GAAAATTCAA | GTTTTAAAAA | GAAAAAAAAA | 300 |

-continued

```
ATTTGCTTAT AGTAAAGTTA CTGAAAAAGA AAAAGTTCTT TCAGAATACC GTAACATGGC      360
TTCCTGGGAC AGGAAGGAAA CCAATGAGAT ACACCCTCCT GACCTCTTAC CAGTACTTCA      420
AAAAGTGCAA TAAAGCTGGT TGAGAGAAAC AAAGAAGTTT CTTTGGAGAC CTACTTTAAA      480
CGCTTAATCC GTGCCAAAAG TCCAAAGTCC ACGAAGCTAA CTACCTTTGG ATGAATTTTC      540
AAGGCAGAGA TAAAATCTCC AATGTGCACT TTAATGACTA ATACTAGTTT TGAGAGACAT      600
TACTACACAT CTATGCTCTG GGACAGACCA AACCTTCAGT CTCTACGTCA ATGGTACAAC      660
AGAGTACTAT TCTCCCCAGT AGTGTTACTG AATTTGCGAC TCACTGAGTT GGAAGAGCTG      720
CTTAAAGGTT TATCATCATC AAAAGCCATT TATTAGGGGG TGTTCTTGTT TTTTTTTGAG      780
CAAAGTGCTA GAAACTCCGT TGTACGTTTC CTACCCCATC ATAGTTTACA ACTTTGTTGG      840
GTAAGATCAA ATGACTCCAA AAAACACCTC TGGAATTTCA ATACAAGTTG CGATAGTTAA      900
GTGCCAAAAC AAGCGGTATG ACAGCTGTCG GGATGCAGAA GTAATCAGTA AAGCCTGGAT      960
CGTGTAAGAA AATGGGGCTT GAGCCAGACT TAAGGAAAG GCCAAGCAGT CAAGAAGGAA     1020
TATGATGTCC AAGGAATATC ATAGGCAGGG TACAGCTGAC AGCAAAGGCA CAGATGCAGC     1080
AACTGTGCCT AGAACCAGTT GATCAGTTTT ATTGCAATAA GAGGTTCATG TAGCCGGGTT     1140
GTGGTAGATA AAAGCAGATA AGTAGACAAA AGCAAGACG GTAGAGAGCC AGACCACAGC      1200
ATTTTGTACT TTATCCTATG AACAGTACAT AGCCAGTGAA GGCTTTATGC CGAGGTAGAT     1260
GACGGATGCA AAGCACAATT TTAGGAAAAT TAATCTGGCA ACTGTGTATA GAAAGGTTAA     1320
TGGAATATCA TCATTGTGGC GAGGTATACA TGTGTCAAAA CTCATCAAAT GTATACACTT     1380
AAAATTGCTG AATTTTACTG CATATAAATT ATACCTCAGG AAGACCAATT TTTTCAAAAC     1440
AAAGGACAAA GATAAAGACA AGAATAAGCA GATTATTAAA ATACAGGCTG GAAAAAAAGT     1500
CAGGCTGTAA AATCCTGAAT ATTTGATAGC TGAGATTAAT TCAAGCCAGC TGATTATACA     1560
CTTTTTTCCC AACTTCAGCA ACATAACACT AGTAGCCTGA GACCAGCCAT GATAGAGTAT     1620
TTATACCTCA GAAATCAGCA AACATTACAA ATCAGGGCTT TATCCCCCCC CCAGGGTGGT     1680
TGTTCAATAT TCACCAGCAC ACCACTGTGT AATTTCTATA CGAGGTTTGG CTTGGATATG     1740
GTGCTAAATG AAGAGTTCCT CGACATTTCT TCTCACTCAA AATAATGACA TAATTCCGAA     1800
GCACCATATC TTAATCTTAC CAGCAGTAGA CAGTTATCAA AAAAGTGTTA AGATTTAAGA     1860
GTCTAACATT TTACTAGTTT CAAGAATTAA AGCATGCCCA TGAATAAGAA ACCTTTGTGT     1920
CTCCCAATCA AGGTTTCTAG CTATTATGTG GTTGGGACT AACACCAACT GATGATGACA      1980
ATGCACAAAA AATTCCACCA TTCATTCCAT TATACTAAAG GCTAATTGCA TGGGCCTATT     2040
ATTGGAATAT GCTTCCTAG TTCAACTAGC TGCATTTCAA TAGAGTAAAG AGGGTTTTCT      2100
GGAGAAACCC TACTGTGAAA AGATGAACTT TGTCTTAACA ACTTTAGTTT CAAAAACTAT     2160
TCATTTATAG ATGCCTATTT CACGTCTCTG AAGCAAAATG GTTCATTTGT TATGTAGATT     2220
ACTAAGCAGT CAGTCACTTA AGAATAAAAA GTTTCTTCTT TAGAGGCTCC AGCTAACTGT     2280
CTGCATAGGT TCAATCTAAA AACCAGCAAA GCATACTGCT AAATATGATA GCAAATAATT     2340
GTTTAAACAC AAATGAGCAC CACCTTCAAA TTTTCCAATC CACTTTCCAA GGGCCAATCT     2400
ATGATTATCC CCAACAAAGA CTGGAGCCCC TCTCTCTCAG AGAAGGAATA CAAAACACAG     2460
GAGAAAGATC ATAAAGAACT ATGTAATATA AGGAGCAGGG AGAAAATGTC AGGTGGGAAA     2520
AATGGCCGGA AATGGGAAGA AGAAACATGT ACAAGAATCA CCAGGAGAGT GACATTCCCC     2580
GCCCCACTGA TACCTAGAGA TTGATTCCCC ATCTTAATGA CTTCTATAAT ATAATCTCAA     2640
GAAAATTCTT GAAACTCAAA TACCTATAAA TCCAGAGGAA AAAGGAAAAG GTAACACATA     2700
```

| | | | | | | |
|---|---|---|---|---|---|---|
| TGCACATATA | AATAATGAAT | TTGCTCTTAT | AAAGAGGTTA | GAACCCACTA | GTCTAAAGCT | 2760 |
| CTAATCATAG | TCTGCTCGTT | CTCCAGTTAT | CTTGCATAAT | TAGAATGGCT | GGCCCCTGCT | 2820 |
| GCTCCCTTTA | CTACTTCAAG | TTCATTAGGC | ATAGCAGGTG | TCAAATATTA | AGTGGCACTA | 2880 |
| ATATCAATTT | AACATTGATT | TCATAAAACT | TAAAAGGGG | AAGAGAATAC | TATACTTCGG | 2940 |
| CCTTTTTAAA | GCAATACATG | CAAAAAGAAA | TAAAGTAACA | GGTTCAAAAT | TACTGTCAAG | 3000 |
| GTTTTATTCT | GAAAAAAGCA | AAACTACAGA | TGGATACACT | AGACAGAATG | CTAAATGCAA | 3060 |
| TCTACATGCA | GAGAACTCTG | CGTTCCAAAA | CAAATGAATA | TGGCTTTATT | CAACTGGGCC | 3120 |
| CAGTTTCCAT | TGTCCCTTTG | GAAGATTTAT | GAGAGGCAGT | ACCCATTATC | TGTTGGAAGT | 3180 |
| TTGATAAAAA | CTTGTATAAA | CAGTGTTTAA | AAAAATCAAA | AAGTAATCTA | AAGAGATATA | 3240 |
| GAAAAATAGT | GTCTTCTTGA | TTGAAATTCT | GCTTAAAAAC | TATACAGAAG | TGTAGTTAAC | 3300 |
| AGGAAAATAC | CTTATTTGAT | AATACGTTCA | AATAGCTATT | ATAAGCTGCC | TGTATTTATT | 3360 |
| ATCTTTATCA | ACATTTAGGA | TGAAAGAAGT | GGGATAAAAA | A | | 3401 |

(2) INFORMATION FOR SEQ ID NO:5:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

GCAGGGAGAA AATGTCAGG                      19

(2) INFORMATION FOR SEQ ID NO:6:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:6:

GTGGAATTC                                9

(2) INFORMATION FOR SEQ ID NO:7:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:7:

GCCAGTGTGG TGGAATTC                        18

(2) INFORMATION FOR SEQ ID NO:8:

(i) SEQUENCE CHARACTERISTICS:
    (A) LENGTH: 25 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:8:

GCTGCTCCCT TTACTACTTC AAGTT 25

(2) INFORMATION FOR SEQ ID NO:9:

(i) SEQUENCE CHARACTERISTICS:
    (A) LENGTH: 22 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:9:

GAAGCAAATG TCGAGGAATC TC 22

(2) INFORMATION FOR SEQ ID NO:10:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:10:

AGGAAAGGAC AGTGGGAGTG 20

(2) INFORMATION FOR SEQ ID NO:11:

(i) SEQUENCE CHARACTERISTICS:
    (A) LENGTH: 22 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:11:

CATTCACCAC ATTGGTGTGC AC 22

(2) INFORMATION FOR SEQ ID NO:12:

(i) SEQUENCE CHARACTERISTICS:
    (A) LENGTH: 33 base pairs
    (B) TYPE: nucleic acid (C) STRANDEDNESS: single
(D) TOPOLOGY: linear (i i) MOLECULE TYPE: cDNA (i i i) HYPOTHETICAL: NO (i v) ANTI-SENSE: YES (x i) SEQUENCE DESCRIPTION: SEQ ID NO:12:

CAGCCTTTTC TATTACAGAC CTTTGTTACA TTG 33

(2) INFORMATION FOR SEQ ID NO:13:

(i) SEQUENCE CHARACTERISTICS:
(A) LENGTH: 31 base pairs
(B) TYPE: nucleic acid
(C) STRANDEDNESS: single
(D) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:13:

CACCACTGTG TAATTTCTAT ACGAGGTTTG G 31

(2) INFORMATION FOR SEQ ID NO:14:

(i) SEQUENCE CHARACTERISTICS:
(A) LENGTH: 25 base pairs
(B) TYPE: nucleic acid
(C) STRANDEDNESS: single
(D) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:14:

GGTACCGAGC TCGGATCCAC TAGTA 25

(2) INFORMATION FOR SEQ ID NO:15:

(i) SEQUENCE CHARACTERISTICS:
(A) LENGTH: 20 base pairs
(B) TYPE: nucleic acid
(C) STRANDEDNESS: single
(D) TOPOLOGY: linear (i i) MOLECULE TYPE: cDNA (i i i) HYPOTHETICAL: NO (i v) ANTI-SENSE: YES (x i) SEQUENCE DESCRIPTION: SEQ ID NO:15:

GACACCTGCT ATGCCTAATG 20

(2) INFORMATION FOR SEQ ID NO:16:

(i) SEQUENCE CHARACTERISTICS:
(A) LENGTH: 18 base pairs
(B) TYPE: nucleic acid
(C) STRANDEDNESS: single
(D) TOPOLOGY: linear (i i) MOLECULE TYPE: cDNA ( i i i ) HYPOTHETICAL: NO ( i v ) ANTI-SENSE: NO ( x i ) SEQUENCE DESCRIPTION: SEQ ID NO:16:

CAAGAATTAA AGCATGCC                                                                       18

( 2 ) INFORMATION FOR SEQ ID NO:17:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:17:

GAATTCCACC ACA                                                                            13

( 2 ) INFORMATION FOR SEQ ID NO:18:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:18:

GTAAGACCAG TCAACAGGGG AC                                                                  22

( 2 ) INFORMATION FOR SEQ ID NO:19:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:19:

CCAGCAAGCT TGCGACCTTG ACCA                                                                24

( 2 ) INFORMATION FOR SEQ ID NO:20:

( i ) SEQUENCE CHARACTERISTICS:
        ( A ) LENGTH: 368 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: mat_peptide
        ( B ) LOCATION: 46..87

-continued ( x i ) SEQUENCE DESCRIPTION: SEQ ID NO:20:

| | | | | | | |
|---|---|---|---|---|---|---|
| GCAGGGAGAA | AATGTCAGGT | GGGAAAAATG | GCCGGAAATG | GGAAGAAGAA | ACATGTACAA | 60 |
| GAATCACCAG | GAGAGTGACA | TTCCCCGCCC | CACTGATACC | TAGAGATTGA | TTCCCCATCT | 120 |
| TAATGACTTC | TATAATATAA | TCTCAAGAAA | ATTCTTGAAA | CTCAAATACC | TATAAATCCA | 180 |
| GAGGAAAAAG | GAAAAGGTAA | CACATATGCA | CATATAAATA | ATGAATTTGC | TCTTATAAAG | 240 |
| AGGTTAGAAC | CCACTAGTCT | AAAGCTCTAA | TCATAGTCTG | CTCGTTCTCC | AGTTATCTTG | 300 |
| CATAATATGA | ATGGCTGGCC | CCTGCTGCTC | CCTTTACTAC | TTCAAGTTCA | TTAGGCATAG | 360 |
| CAGGTGTC | | | | | | 368 |

What is claimed is:

1. A method of detecting mRNA transcripts of the CATR1 gene in a tissue sample comprising the following steps:
   (a) isolating RNA comprising mRNA from the tissue samples;
   (b) amplifying CATR1 mRNA by a reverse transcriptase-PCR procedure using at least one primer which anneals to the sense strand of the CATR 1 gene and at least one primer which anneals to the antisense strand of the CATR1 gene; and
   (c) detecting the presence or absence of a CATR1 primer specific amplified product
      wherein the presence of said CATR1 amplified product is indicative of the presence of mRNA transcripts of the CATR1 gene.

2. The method of claim 1 further comprising the step of quantifying the amount of the CATR1 primer specific amplified product.

3. A primer which specifically amplifies CATR1 mRNA transcripts consisting of a nucleic acid molecule that anneals to a region on at least one strand of the CATR 1 gene.

4. The primer of claim 3 wherein the primer comprises from about 15 to about 30 nucleotides.

5. The primer of claim 3 wherein the primer has a combined guanine and cytosine content of greater than 40%.

6. The primer of claim 3 wherein the primer is complementary to a region on the sense strand of the CATR1.3 genetic element.

7. The primer of claim 3 wherein the primer is complementary to a region on the antisense strand of the CATR 1.3 genetic element.

8. The primer of claim 4 wherein the primer comprises the sequence 5'-GCAGGGAGAAAATGTCAGG-3'; SEQ.ID.NO. 5.

9. The primer of claim 4 wherein the nucleic acid molecule comprises the sequence 5'-GACACCTGCTATGCCTAATG-3'; SEQ.ID.NO. 15.

10. An isolated tumor suppressor gene CATR1.

11. The tumor suppressor gene of claim 10, wherein a segment of the gene encodes a peptide having the amino acid sequence of SEQ.ID.NO. 3.

12. The tumor suppressor gene of claim 10, wherein the gene comprises the nucleotide sequence of SEQ. ID. NO. 2.

13. The tumor suppressor gene of claim 10, wherein the gene comprises the nucleotide sequence of SEQ.ID.NO.4.

14. An isolated and purified DNA molecule consisting of a nucleotide sequence of, or complementary to, one of the strands of the double-stranded CATR1 gene located on the q arm of chromosome 7 at band 31-32.

15. An isolated 1.3 kb nucleic acid molecule which encodes the amino acid sequence of SEQ. ID. NO 3.

16. The 1.3 kb nucleic acid molecule of claim 15 wherein the molecule comprises the nucleotide sequence of SEQ. ID. NO. 1.

17. An isolated segment of the CATR1 gene comprising the nucleotide sequence of SEQ. ID. NO. 2.

18. The nucleic acid molecule of claim 15 wherein the nucleic acid is DNA.

19. The nucleic acid molecule of claim 15 wherein the nucleic acid is mRNA.

* * * * *